(12) United States Patent
Marnø et al.

(10) Patent No.: US 8,530,844 B2
(45) Date of Patent: Sep. 10, 2013

(54) RECORDING OF POSITION-SPECIFIC WAVELENGTH ABSORPTION SPECTRA

(75) Inventors: Henrik Marnø, Hellerup (DK); Klavs Martin Sørensen, Brønshøj (DK)

(73) Assignee: SFK Technology A/S, Herlev (DK)

( * ) Notice: Subject to any disclaimer, the term of this patent is extended or adjusted under 35 U.S.C. 154(b) by 988 days.

(21) Appl. No.: 11/993,195

(22) PCT Filed: Jun. 27, 2006

(86) PCT No.: PCT/DK2006/000380
§ 371 (c)(1),
(2), (4) Date: May 28, 2010

(87) PCT Pub. No.: WO2007/000166
PCT Pub. Date: Jan. 4, 2007

(65) Prior Publication Data
US 2010/0233329 A1    Sep. 16, 2010

(30) Foreign Application Priority Data

Jun. 27, 2005 (DK) ................................. 2005 00952

(51) Int. Cl.
*G01N 21/35* (2006.01)
(52) U.S. Cl.
USPC ....................................................... 250/341.2
(58) Field of Classification Search
CPC ........................... G01N 21/01; G01N 21/3563
USPC ....................................................... 250/341.2
See application file for complete search history.

(56) References Cited

U.S. PATENT DOCUMENTS

| 3,493,774 A | 2/1970 | Knudsen |
| 3,805,072 A * | 4/1974 | Goerens et al. ............... 250/342 |
| 3,877,818 A | 4/1975 | Button et al. |
| 4,078,313 A | 3/1978 | Hennessy |

(Continued)

FOREIGN PATENT DOCUMENTS

| EP | 0 402 877 A1 | 12/1990 |
| EP | 1 233 260 A1 | 8/2002 |
| GB | 2 179 443 A | 3/1987 |
| JP | 63 085430 | 4/1988 |
| JP | 02 016434 | 1/1990 |
| JP | 10 267732 | 10/1998 |

(Continued)

OTHER PUBLICATIONS

Swatland, H.J. (2002) Modulation of the optical path through pork using sliding needles. Food Research International. 35:347-350.

*Primary Examiner* — Constantine Hannaher
(74) *Attorney, Agent, or Firm* — Knobbe, Martens, Olson & Bear LLP

(57) ABSTRACT

The invention relates to recording of position-specific optical measurements of substances such as foodstuff, building materials, combustion products etc. The invention provides online, in-situ recording of wavelength absorption spectra in substances, performed without removing a sample from the substance. In inhomogeneous products, the position correlated to each spectrum allows for extraction of both average values for larger regions as well as specific values characteristic for smaller individual portions. In a preferred embodiment, a probe with two elongate arms has light guiding and light collecting means for recording infrared absorption spectra of portions between them, as well as means for determining an insertion distance into the product. The invention may be applied to as different substances as diary products (cheese, cream, milk), fruit, berries, seeds, meat, vegetable and animal fat, animal feed, water, wine, beer, lemonades, oils, rubber and plastic materials, gypsum and plaster, cement and concrete mixes, paints, glues etc.

26 Claims, 8 Drawing Sheets

(56) References Cited

U.S. PATENT DOCUMENTS

| | | | |
|---|---|---|---|
| 4,270,274 | A | 6/1981 | Hennessy |
| 4,352,245 | A | 10/1982 | Hennessy et al. |
| 4,825,711 | A | 5/1989 | Jensen et al. |
| 5,044,755 | A | 9/1991 | Landa et al. |
| 5,705,815 | A * | 1/1998 | Heesch ............ 250/341.2 |
| 6,563,580 | B1 * | 5/2003 | Aignel et al. ............ 356/300 |
| 6,587,702 | B1 | 7/2003 | Ruchti et al. |
| 6,859,282 | B1 | 2/2005 | Callow et al. |

FOREIGN PATENT DOCUMENTS

| | | |
|---|---|---|
| WO | WO 80/01205 | 6/1980 |
| WO | WO 92/21025 | 11/1992 |
| WO | WO 93/24832 | 12/1993 |
| WO | WO 97/25609 | 7/1997 |
| WO | WO 99/19727 | 4/1999 |
| WO | WO 00/02043 | 1/2000 |
| WO | WO 01/23868 A1 | 4/2001 |

* cited by examiner

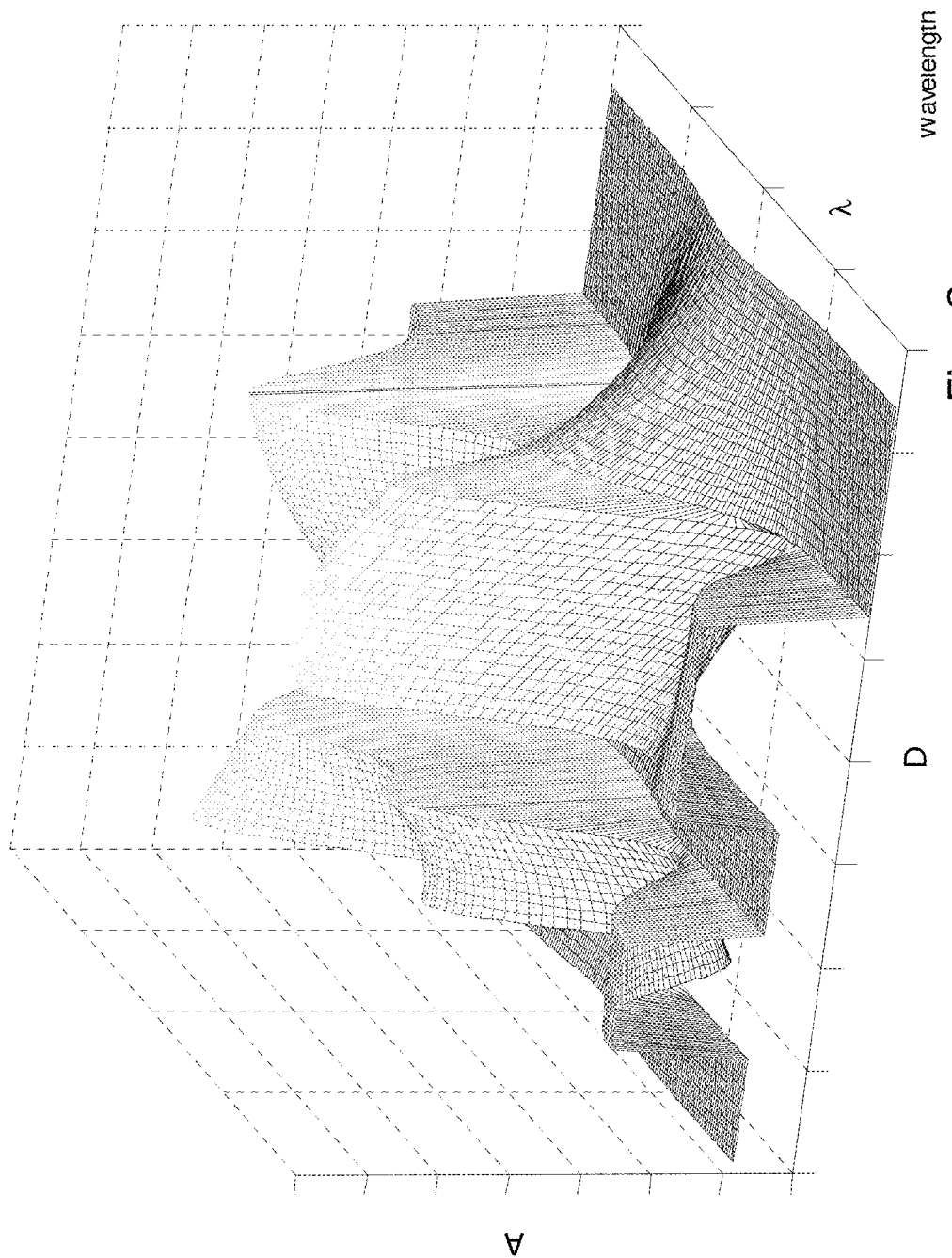

RECORDING OF POSITION-SPECIFIC WAVELENGTH ABSORPTION SPECTRA

CROSS REFERENCE TO RELATED APPLICATION

This application is a US National Phase of PCT Application Number PCT/DK2006/000380, filed on Jun. 27, 2006, designating the United States of America and filed in the English language, which claims priority to Danish Patent Application No: 2005 00952, filed Jun. 27, 2005. The disclosures of the above-referenced applications are hereby expressly incorporated by reference in their entireties.

FIELD OF THE INVENTION

The invention relates to the recording of optical measurements for characterizing a substance. In particular, the invention relates to recording a multitude of wavelength absorption spectra at different locations in an inhomogeneous substance to determine spatial average/mean values of parameters in the substance.

BACKGROUND OF THE INVENTION

In the fabrication of various products, it is often important to determine qualitative and/or quantitative parameters of used substances in order to control the formation process and ensure a high quality of the end product. When detailed knowledge of the composition is required to determine the parameters, optical absorption spectroscopy such as near infrared transmission (NIT) spectroscopy provides a precise and efficient approach.

In order to extract valid data, a statistically significant amount of data should be obtained, corresponding to measurements on multiple samples. Extraction of representative samples can sometimes be difficult and at other times destroy the product.

Many products are formed by or involve substances which are inhomogeneous somewhere along the process of formation. The extraction of samples and determination of parameters are made impediment if the substance is inhomogeneous. A number of different examples where this situation occurs will be given here.

- In processes of fermentation for production of e.g. beverages, medicine, dairy products etc., the liquid culture is typically inhomogeneous at some stages of the fermentation. The liquid culture can settle in layers having different compositions.
- Cheese will often have a solidity more like a gel or a solid, where different parts of the substance are definitely not miscible. Due to the lack of miscibility, such products often have a pronounced different state or composition at its surfaces than in the centre.
- Most fruits and berries are inherently inhomogeneous.

In these examples, the inherent inhomogeneities make it difficult to extract a representative sample for characterization. Previous solutions to this problem include extracting samples followed by homogenization (e.g. liquefaction) followed by spectroscopy. In fermentation processes, fermentors may include a column for circulation wherein a fixed absorption spectrometer performs measurements on liquid flowing past it.

Also, for homogenous or almost homogeneous substances, achieving a statistically significant amount of data may be troublesome as the extraction of numerous samples can be difficult. One example of this is very reactive substances or solutions which require a controlled environment. Another example is solid or near-solid substances where removal of samples is not desirable. Here, extraction of samples for analysis may be extremely difficult. At the same time, measuring at a single position or sample in the substance will not provide the required amount of data.

Classification of inhomogeneous substances based on spectroscopy is difficult because the inhomogeneity makes representative data difficult. Previous solutions to this problem include measurements on flowing liquids such as e.g. cytometry and the like. However, it is not always practical, and often very expensive, to incorporate a flow section for the only reason of performing measurements. Besides, this is only applicable to fluid substances.

Unprocessed meat products are typically inhomogeneous, and a number of photometric methods for measuring geometrical parameters inside meat products such as a position of a fat/meat interface or the ratio of fat/meat have been described. Although the photometric measurement is correlated with a measurement of insertion depth, these methods only obtain a reflectivity value and no spectral information. Some of these are WO 80/01205, U.S. Pat. Nos. 4,352,245, 4,270,274, 4,825,711, 6,859,282, EP 668 999, GB 2 179 443, and WO 92/21025. All of these apply near infrared reflection (NIR) measurements using an invasive probe in order to determine the fat/lean meat interface or ratio in the meat product. It is a disadvantage of these methods that they can not obtain spectroscopic data and can therefore not be used to extract detailed information of the chemical composition.

JP 02016434 discloses a device for determining the quality of foodstuff products such as fruits or vegetables. Here, two optical fibre tips (41a and 51a) are inserted to a position determined by the stop 42. The intensity of the transmitted/reflected light is recorded by a photomultiplier tube 61. This method does not obtain spectroscopic data and does not measure different portions of the product.

Methods actually recording a spectrum inside a meat product have been described, e.g. EP 402 877, WO 99/19727 and U.S. Pat. No. 6,563,580 (also published as WO 00/02043). However, these methods only record a spectrum of a single portion of the product, and do not give repeated measurements at different positions in the product.

SUMMARY OF THE INVENTION

The present invention solves the problem of recording representative NIT spectroscopic data of inhomogeneous substances which can be used in classifying the inhomogeneous substances by providing a method for recording a plurality of consecutive NIT spectra in a substance as a function of position.

It is therefore an object of the invention to provide a method and an apparatus for recording optical absorption spectra at multiple positions in, or of multiple portions of, a substance.

It is another object of the invention to provide a method and an apparatus for determining mean or average values of qualitative and/or quantitative parameters in inhomogeneous substances without the need for extracting samples of the substance.

It is another object of the invention to provide a method and an apparatus for determining values of qualitative and/or quantitative parameters for different parts of a substance without the need for extracting samples of the substance.

In the present context, a substance is any material composition such as liquids, gels, granulates, powders, foams, cuttable solids, etc. In particular, substances refer to intermediates, semi-manufactures, substrates or matrices in processes of manufacturing, preparation or processing e.g. at plants or factories where it is of interest to classify, grade or characterize incoming, intermediate or outgoing products. The invention may be applied to as different substances as dairy products (e.g. cheese, cream, butter, milk, yoghurt, etc.), chocolate, cocoa butter, fruit, berries, seeds, meat, vegetable and animal fat, animal feed, water, wine, beer, lemonades, oils, rubber and plastic materials, gypsum and plaster, cement and concrete mixes, paints, glues, medicaments, etc.

In a first aspect, the invention meets the above objects by providing a method for recording position-specific wavelength absorption spectra, the method comprising the steps of:

providing a probe with light guiding means and light collecting means positioned in an optical path of light to be transmitted by the light guiding means, introducing the probe in a substance to position an interior portion of the substance in said optical path between the light guiding means and the light collecting means, recording consecutive spectra at consecutive positions in the substance by performing the following steps a multitude of times in a consecutive manner:

recording a wavelength absorption spectra of light transmitted through the interior portion currently in the optical path to the light collecting means;

changing the position of the probe in the substance and thereby changing the interior portion of the substance in the optical path;

determining a position and/or a change in position of the probe in the substance.

The consecutive steps need not be performed in the given order.

In a second aspect, the invention meets the above objects by providing an apparatus for use in performing the method according to the first aspect, i.e. an apparatus for recording position-specific wavelength absorption spectra. The apparatus comprises a probe comprising light guiding means and light collecting means positioned in an optical path of light to be transmitted by the light guiding means, the probe being shaped so that the introduction of the probe in a substance will position an interior portion of the substance in said optical path between the light guiding means and the light collecting means and so that changing the position of the probe in the substance will change the interior portion of the substance in said optical path a light source for providing infrared light of multiple wavelengths to the light guiding means, a detecting unit for receiving light collected by the light collecting means and for detecting and recording wavelength absorption spectra of the received light at different consecutive positions of the probe, means for determining, during introduction or extraction of the probe, a plurality of consecutive positions and/or changes in the position of said probe in the substance, and means for correlating the determined consecutive positions or changes in position with consecutive wavelength absorption spectra recorded by the detecting unit.

The position of the probe in the substance is preferably the position of the optical path in the substance. The position may e.g. be an insertion distance into the substance from a point of insertion at a surface part of the substance. Determining a position may include determining a distance from an exterior fixed point of reference to the optical path between the light guiding means and the light collecting means. The determined position may be a number or a sequence being indicative of a distance. In one embodiment, the means records a change in an external parameter in comparison to a clock signal whereby a position can be calculated for a given time indication.

As specified, the method and apparatus record consecutive spectra of different portions of the substance during introduction or extraction. Therefore, the apparatus must be able to determine a plurality of consecutive positions during each introduction or extraction, and not simply one position for each introduction. As a result, a series of consecutive spectra from consecutive positions is recorded which provides a representative set of spectra for analysis of the substance, regardless of whether the object of the analysis is to obtain average values or to identify variations to be analysed separately.

In a preferred implementation, as many as 100 sets of correlated spectra and positions are recorded per centimeter during extraction of the probe, resulting in up to 1,000 data sets for an insertion depth of 10 cm. The preferred sampling rate (number of sets recorded per centimeter) depends on the nature of the foodstuff product and the object of the analysis. For inhomogeneous substances whose composition varies over a scale of less than one centimeter, a large sampling rate is required in order to obtain statistically representative data for each sub-segment in the substance. In a preferred embodiment, the number of sets of correlated spectra and positions recorded are larger than 5/cm, larger than 10/cm or larger than 25/cm, or preferably larger than 50/cm.

Also, the apparatus is configured to correlate a position with a recorded wavelength absorption spectrum. Thereby, each recorded intensity is related to two variables, a wavelength (or frequency) and an indication of position such as insertion depth. The fact that each wavelength absorption spectrum is associated with a position is a novel and unique feature of the present invention. The recorded spectra may be presented in a three-dimensional coordinate system with the absorption or transmission shown as a function of wavelength and insertion depth. Substances formed by different layers having a given thickness and the recording of several spectra within each layer can be used to segment the recorded spectra corresponding to each layer. As the composition within a region or a layer may be substantially homogeneous, the recorded spectra may, although recorded at different positions, represent repeated measurements of absorption spectra within the region or layer and thus provide a good statistical basis for prediction models for a particular region or layer.

When receiving light from the light source, the light guiding means transmits the light from the probe at a position and in a direction so that the light propagates along a first optical path intersecting the light collecting means. The light collecting means is formed to collect at least light propagating along the first optical path and guide it towards the detecting unit. The light collecting means is thereby preferably positioned opposite to the light guiding means in the probe. Both the light guiding and collecting means may comprise optical components such as lenses, collimators, mirrors, optical fibres, prisms, windows, gratings, holograms, splitters, couplers, etc.

The light source preferably has an emission spectrum ranging from 800 nm to 3,000 nm or at least spectrum having a uniform intensity in the intervals 1,000-1,150 nm, 1,650-1,750 nm 1,900-1,980 nm, and 2,250-2,350 nm. These intervals are relevant when determining parameters related to the protein, water and fat content in the product. In the fermentation process of e.g. beer or wine, determination of carbohydrates is important and carbohydrates have strong absorbance bands at 1,440 nm, 1,520 nm, 1,580 nm, 2,080 nm and 2,200 nm.

Consequently, the detecting unit can detect and record light in the same ranges and intervals.

The probe is preferably inserted into the substance in situ so that no sample is removed from the substance. In an alternative formulation, portions of the substance traversed by the optical path in the recording of a spectrum are not separated from the remaining substance, and these portions will continue to form a part of the substance after the recording of spectra. Hence, no sample of the substance is extracted and the entire process is carried out at the original or natural place or site of the substance, e.g. conveyor lines at dairy plants.

Previously, wavelength absorption spectra of various substances have typically been recorded in a laboratory using liquefied samples. The invention presents a breakthrough within the field in that it may determine such parameters from in-situ recording where no sample need to be removed from the product.

Systems for characterizing products on a conveyor line can be characterised as:
- inline/online meaning that the measurements is performed on or in the product (i.e. without removing a sample) and that the parameter is available immediately or shortly after the measurement;
- at-line meaning that a sample is extracted from the product and analysed at or near the product line, the parameter is available when the sampled product has moved further down the product line; or
- offline meaning that a sample is extracted from the product and analysed at another location, e.g. a centralized laboratory. The parameter is first available at a later time.

Traditionally, the characterization has been based on absorption spectra recorded in laboratories using samples from a limited number of products. Thereby, the resulting characterization was not associated with a specific product, but rather with a batch of products e.g. from a specific supplier. In a preferred embodiment, the apparatus may be interfaced with a data-merge system and configured to perform online absorption spectra-based characterization or classification of substances. Here, the characterization is available shortly after extraction of the probe. The online characterization allows for immediate characterization of the product by sorting of products or by marking product using e.g. tag encoding, stamping or associating the characterization with the product in the plant automation system.

As described previously, recordings of wavelength absorption spectra according to the prior art have been carried out using liquefied or homogenised samples extracted from the products. Thereby, the result did not give any indication of the distribution of the monitored substances in the product—information which may be crucial for the estimation of the state or quality of the product. In the apparatus of the present invention, the processor may be configured to provide the qualitative and/or quantitative parameters as a function of position. This is advantageous as it provides very valuable information of e.g. the distribution of substances in the product.

In a preferred embodiment, the method further comprises comparison of recorded spectra with wavelength absorption spectra from an internal database, e.g. using a model such as a parafac model. The spectra in the database have been recorded previously on substance portions with known qualitative and/or quantitative parameters and have been calibrated against laboratory data. Thereby, corresponding parameters of the portion(s) used in the recording may be determined.

For this purpose, the apparatus may further comprise a data processing unit for receiving recorded spectra and being configured to determine qualitative and/or quantitative parameters of the substance. The data processing unit comprises a memory for holding a database of previously recorded spectra. The data processing unit also holds means (such as software) for comparing recorded spectra with spectra from the database to identify at least approximate parameters of the portions of the substance used in the recording.

In order to provide a statistical foundation, the method may also involve pre-processing of recorded spectra to sort the spectra into segments which are relevant to the parameters to be determined. Spectra in each segment may then be merged, or mean values may be formed, so that spectra in a segment are used to represent repeated recording in the corresponding portions. Each segment may correspond to one or more regions or position ranges in the substance, in which case spectra are sorted according to their correlated position. As a result, parameters may be determined for individual segments instead of for individual portions. This provides a determination of more precise and/or representative parameters for characterising different parts or compositions of the substance. The parameters from individual segments may then be used to determine an overall classification of the substance. In the apparatus, the data processing unit can be configured to carry out these tasks as well as to presenting them to the user.

In order to determine transmission or absorption spectra, the apparatus may need to record reference spectra at regular intervals. Also, calibration spectra may be recorded for checking or adjusting the accuracy of the apparatus by comparison with a standard instrument. For these purposes, the detecting unit of the apparatus may be configured to record a spectrum of light received from the light collecting means at user determined intervals when the means for determining a position indicates that there is no interior portion of the substance in said optical path. Such recorded spectra may be used for reference or calibration purposes.

In a preferred embodiment, the probe comprises a first oblong or elongate probe arm holding the light guiding means and a second oblong or elongate probe arm holding the light collecting means, the first and second probe arms extending in parallel from a common base. Each probe arm may have a point for penetrating the surface of the substance and a first cutting edge starting at the point.

To determine quantitative parameters from the recorded spectra, it is preferable that there is an at least substantially constant distance between the probe arms. For this reason, the cutting probe is preferably formed in a material composition and dimensioned to ensure a constant distance between the light guiding means and the light collecting means during insertion in the substance.

The dimensioning refers to the thickness of the material used, the length of the probe and the specific shape of the probe. In the case of two parallel extending probe arms, the dimensioning refers to the circumference, shape and length of each probe arm. Typically, the probe is formed in a metal alloy such as stainless steel and the probe arms are rods with interior lumens for holding optical fibres. In one embodiment, the probe has a cross-bar between the probe arms to ensure that the probe arms are not deflected during insertion. In these and similar cases, the shape and size of cross-bars and thickness of the lumen walls are also part of the relevant dimensioning.

The basic idea of the invention is to record position-specific absorption spectra, in order to be able to characterize substances such as foodstuff products without removing a sample from the product. It is an advantage that the invention can be applied to inhomogeneous products as well, since the position correlated to each spectrum allows for the extraction of both average values for larger regions as well as specific values characteristic for smaller individual portions. Also, it is the principle of the invention that the recording and processing of data are performed online and in-situ, thereby allowing for an online characterization or classification of the substances.

It is another advantage that the invention allows for all products or substances in a fabrication line to be characterized, instead of only performing random checks. Since no sample is removed from the substance, the recording of the absorption spectra has not damaged the substance or its value. Thereby, all substances in a fabrication line can be measured upon without any decrease in value.

In a preferred embodiment, the invention provides a method and an apparatus for performing Near-Infrared Transmission (NIT) spectroscopy in multiple portions of a substance. The method and the apparatus according to the invention may also be used to determine the thickness of various layers, average occurrence or size of domains, particle sizes.

These and other aspects of the invention will be apparent from and elucidated with reference to the embodiments described hereinafter.

BRIEF DESCRIPTION OF THE FIGURES

FIG. 8 is a three-dimensional graph showing wavelength absorption spectra recorded at multiple positions.

The figures are not to scale.

DETAILED DESCRIPTION OF THE INVENTION

Figure 1:
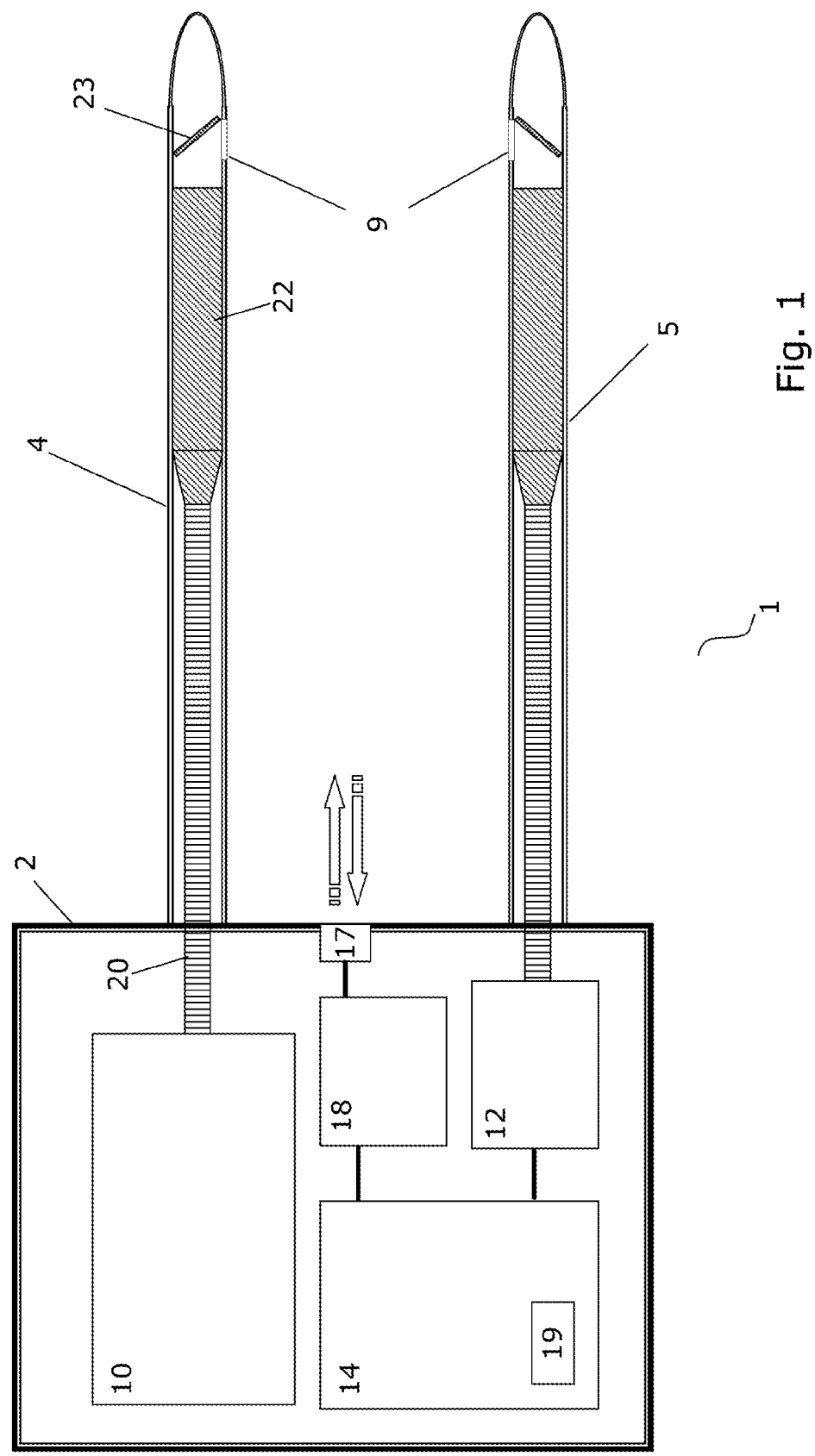
FIG. 1 is a schematic drawing of an apparatus according to an embodiment of the invention.

In the following, a preferred embodiment of the invention will be described in relation to FIGS. 1-3. In FIG. 1, an apparatus 1 for recording of wavelength absorption spectra is shown. The apparatus has a casing 2 and two probe arms 4 and 5 extending in parallel, each probe arm having a transparent window 9 through which light can be transmitted or received. The casing holds a light source 10 for providing light of multiple wavelengths to the light guiding means in probe arm 4. A broadband optical fibre 20 receives and transmits light from the light source 10 to a collimator 22 which forms directional light deflected by mirror 23 and transmitted by window 9. These components provide the light guiding means. The light source can e.g. be a Tungsten lamp emitting a broad thermal spectrum including the wavelength range 1000-3000 nm or a tunable laser. Similar components in probe arm 5 provide light collecting means for receiving light emitted from probe arm 4 and guiding it to detecting unit 12. The detecting unit 12 may be a spectroscope recording light intensity as a function of wavelength (or frequency).

The means for determining a position of the probe in the substance is here embodied by a wireless distance-determining device 17 providing a signal to a position calculation unit 18 for determining the position or a change in position.

The spectra from detecting unit 12 and the correlated positions from position calculation unit 18 are collected by a data processing unit 14. The data processing unit includes a processor and memory 19 holding software to be executed by the processor and databases with previously recorded spectra. In another embodiment (not shown), the data processing unit 14 and memory 19 are located external to the casing 2. In this embodiment, the data processing unit 14 may e.g. be a personal computer connected to the casing 2 by a cable.

Figure 2:
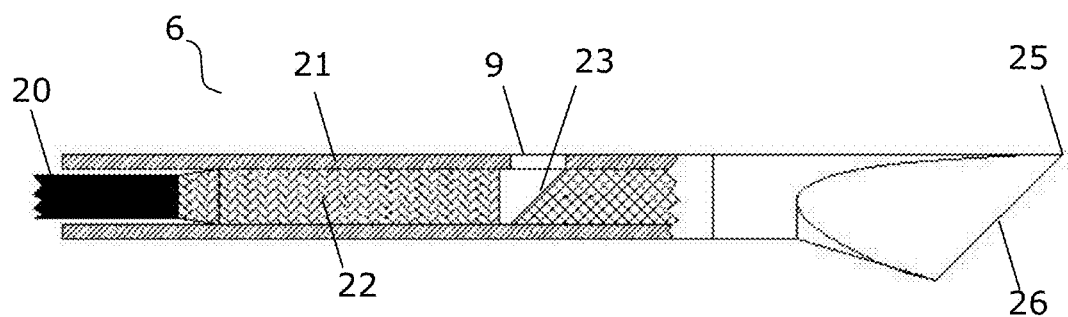
FIGS. 2 and 3 are cross-sectional views of different probes.

FIG. 2 shows another embodiment of probe arms 4 and 5. The probe arm 6 shown in FIG. 2 is designed to penetrate harder substances such as cheese, fruit, bread, meat and powders. Here, the probe arms must be strong enough not to deflect when inserted in the substance. For this purpose, the probe arm is formed in a strong metal tube 21 and equipped with a tip having a penetrating point 25 and a cutting edge 26. The probe arm includes the light guiding or collecting means similar to probe arm 4 and 5 on FIG. 1.

Figure 3:
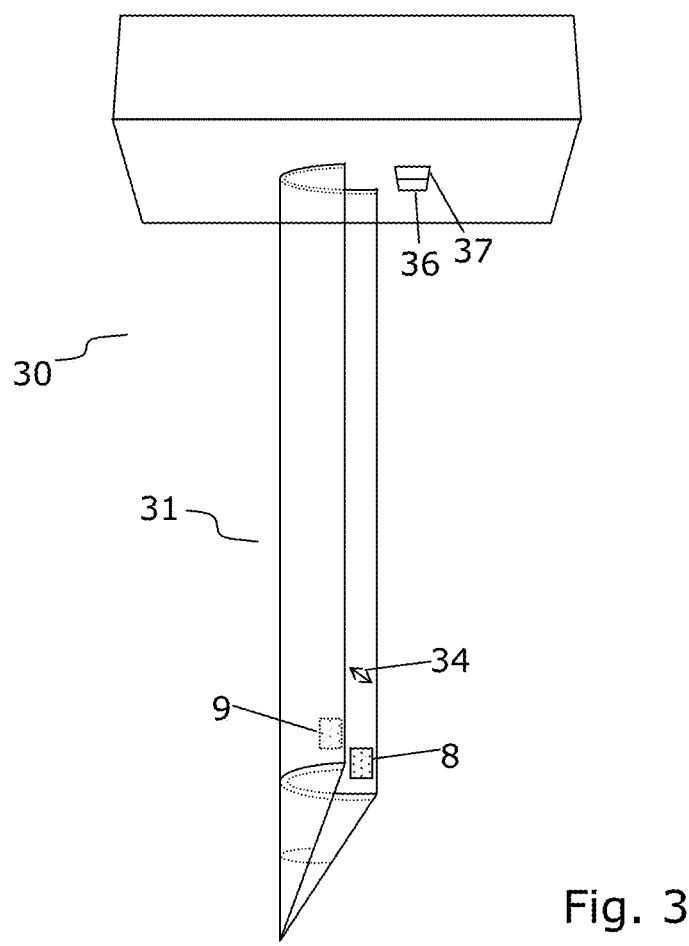

An alternative probe 31 is shown for apparatus 30 in FIG. 3. Here, the probe is in one piece with the form of a half-pipe, optionally with a sharp point and cutting edges. Probe 31 has oppositely positioned windows 8 and 9 through which light is transmitted and collected. An inner diameter 34 of the half-pipe determines the distance between windows 8 and 9 and thereby the length of the optical path of light in a portion of the substance. The light guiding and light collecting means of probe 30 can be formed in relation to windows 8 and 9 by optical components similar to those shown for probe arms 4 and 5 in FIG. 1.

Since probe 31 is formed in one piece, the risk of misaligning windows 8 and 9 by deflecting a probe arm is removed. In preferred embodiments, both of probe arms 4, 5, 6, and 30 are designed to be waterproof and easy to sterilize and having smooth outer surfaces.

Figure 4:
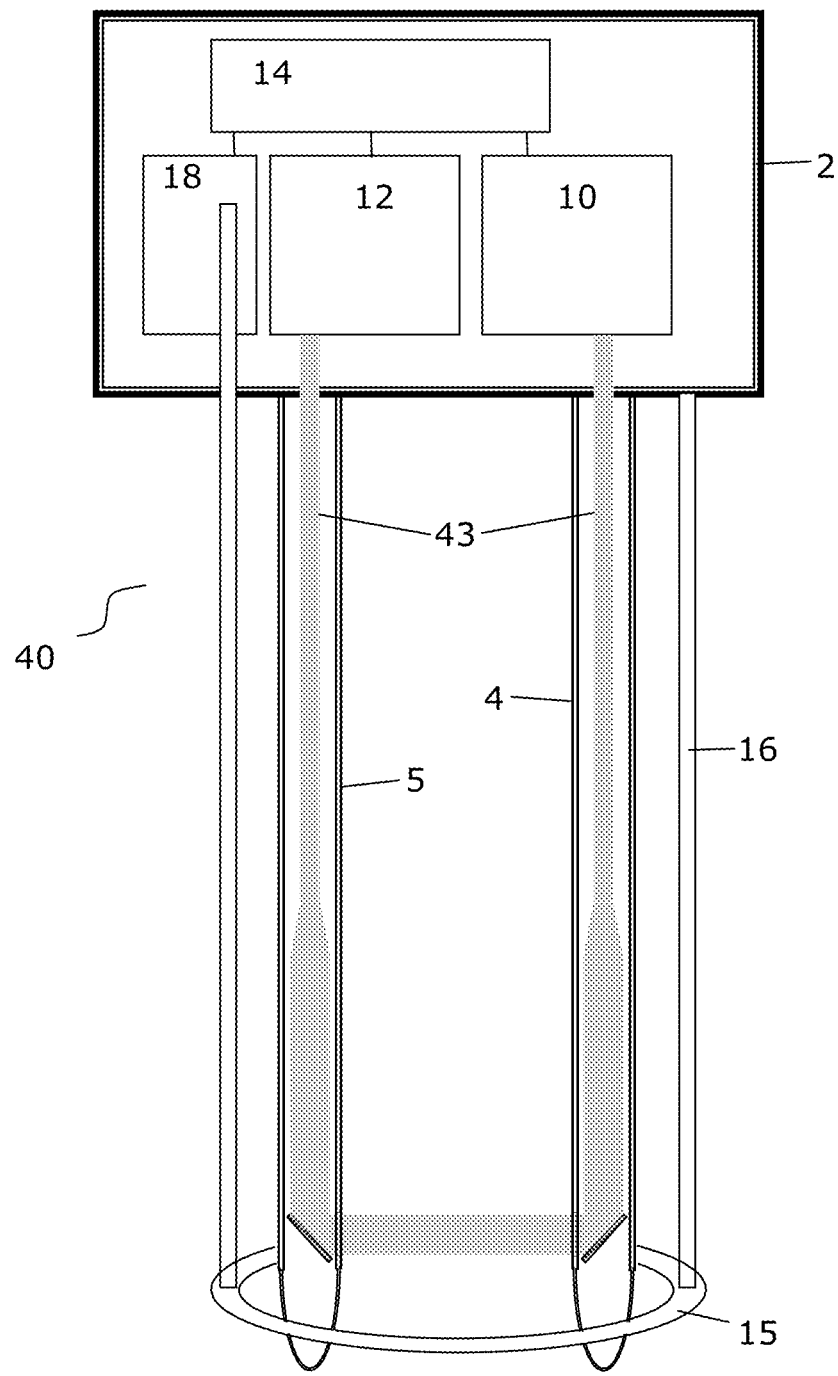
FIG. 4 is a cross-sectional view of the apparatus shown in FIG. 1, illustrating the optical path.

FIG. 4 shows the optical path 43 of light in the apparatus 40, and will be described using references to details in the probe arms 4 and 5 shown in FIG. 1. The optical path in probe 30 of FIG. 3 is similar. The apparatus 1 holds a light source 10 for providing infrared light of multiple wavelengths to the light guiding means in probe arm 4. The light source is a Tungsten lamp emitting a broad thermal spectrum including the wavelength range 1000-2500 nm. Broadband optical fibre 20 receive and transmit light 43 from the light source to collimator 22 which forms directional light 43 deflected by mirror 23 and transmitted by window 8.

Light 43 transmitted by matter interspacing windows 8 and 9 will be collected by the light collecting means in probe arm 5. Light transmitted by window 9 and incident on mirror 23 will be received by collimator 22 that couple the light 43 to broadband optical fibre 20. Fibre 20 transmits light to a detecting unit 12 for detecting and recording absorption spectra. The detecting unit may be a spectroscope.

In the following, different embodiments for the means for determining a position of the probe in the substance are described.

Apparatus 1 shown in FIG. 1 and apparatus 30 shown in FIG. 3 apply wireless (e.g. optical or sonic) means for determining position. Here, an emitter 36 can emit an optical or a sonic signal which is reflected by a surface or layer of the substance. Receiver 37 receives the reflected signal, and a distance or a change in distance can be calculated. Products for optical, sonic or other wireless distance measuring, e.g. infrared distance measuring sensors, are commercially available.

Apparatus 40 in FIG. 4 applies mechanical means for determining insertion depth, parts of which are shown in FIG. 1. Here, ring 15 abuts the surface of the substance upon insertion of probe 31, and rods 16 are pushed into the apparatus casing 2. A position calculation unit 18 determines the movement of rods 16 and calculates a position in the form of an insertion depth of the probe into the substance. Any type of commercially available linear position sensor may be used for this purpose.

In an embodiment adapted for use on solid substances, the means for determining position comprises a step motor operating on the rods 16 and ring 15 which acts as a support for abutting an exterior portion of the substance. The probe is first inserted into the substance, either manually or by a machine, whereafter the step motor performs a stepwise extracting by pushing ring 15 away from the casing 2. This provides a very precise extraction of the probe, ensuring that spectra can be recorded at regular intervals. Some slack in the extraction may be experienced due to elasticity in the substance, but this may be accounted for by disqualifying the first one or more millimeters or centimeters.

Figure 5:
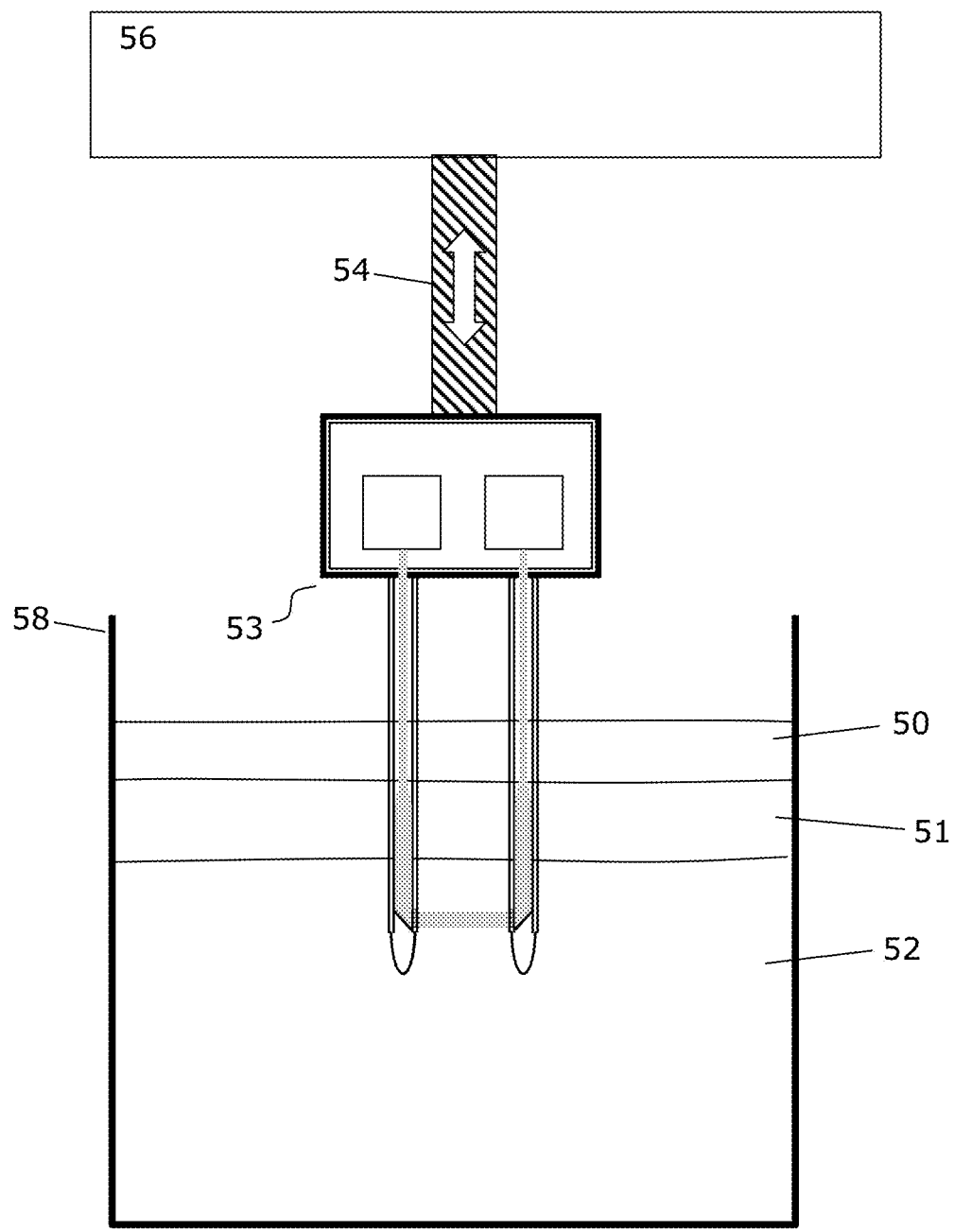
FIG. 5 illustrates the use of the apparatus according to the invention to measure mean values of an inhomogeneous, layered liquid.

Apparatus 53 in FIG. 5 is similar to apparatus 1 of FIG. 1, but it is mounted on a movable member 54 of a fixed support 56. Here, the means for determining position of the probe in the substance is calculated by having a fixed relation between fixed support 56 and vat 58. By controlling the movement of member 54, the position and change in position of the probe can be determined when the dimensions of the system are known.

The spectra from the spectroscope and the correlated positions are collected and correlated by means for correlating incorporated in the data processing unit 14.

The means for correlating position with recorded spectra depends on the embodiment of the means for determining position, and will typically be implemented in the data processing unit as software or an ASIC. In the embodiment applying a step motor, the correlating means provide trigger pulses to both the spectrometer and the step motor, to ensure the recording of a wavelength absorption spectrum for every extraction step of the probe. Numbering of the spectra and knowledge of the step size then provides the correlation between position and spectra. In the embodiments without step motor, the correlating means can e.g. be based on time stamps on recorded spectra and the positions determined by the mechanical or optical means for determining position.

The application of the method and apparatus according to the invention will now be described for five different situations. Thereafter, a detailed example of data processing will be given in relation to one of these situations.

Wine

In order to produce a high quality wine it is vital to determine the quality from harvest to fermentation and finally to blending and bottling. Prior to and during the harvest of grapes, the chemical quality of the grapes in terms of content of glucose, fructose, sucrose, organic acids etc. can be determined by the apparatus in the following way. A sample of the grapes is collected in a stainless steel cylinder and the apparatus equipped with sharp knives is pressed through the grapes thus providing the chemical composition of a known number of individual grapes. In order to obtain representative and valid information of the quality of the grape sample an average is calculated. Present information can be used to estimate the optimum harvest time and when delivered to the winery, each batch of grapes can be sorted according to uniform quality. The information may also serve as a payment grid to the grape farmer.

During fermentation carbohydrates in the grapes is fermented mainly to ethanol by the natural yeast present in the grapes. FIG. 5 shows a fermentation vat 58 with different layers 50-52 of liquid substance. In this process, the apparatus can be used to determine vital chemical components such as glucose, fructose, sucrose, organic acids, ethanol, $CO_2$ etc. Consequently, the winery is able to obtain on-line vital information during the process and act according to this information. Consequently, the chemical determination can be made online without the need for sending a grape sample to a centralized laboratory. The quality of the final wine can be used to estimate possible blending of final wines before bottling.

Rice

Harvested rough rice is first transported to rice-drying facilities, where the moisture content of the rough rice is checked at reception. After moisture content inspection, the damp rough rice is dried out whereafter the hulls are removed. Next, the rice is transported to rice-mill facilities, where the bran layers and germs are removed. Components of brown rice such as sound whole kernel, immature kernel and underdeveloped kernel, are important for assessing the quality of rice. An inspector usually visually evaluates the components of the brown rice prior to milling. The major chemical constituents of milled rice are moisture (15%), protein (7%) and starch (77%). The protein content of milled rice is a very important quality aspect.

Thus measuring moisture and protein content in rice is an essential task when grading rice. Instead of taking samples to a dedicated spectroscopic instrument, it would be advantageous to perform the measurement in the containers holding the rice. The present invention allows in situ recording NIT spectra of rice at many different portions in a simple and fast procedure, thereby providing representative spectroscopic data for determination of moisture and protein content.

Vegetable oil

For the vegetable oil industry, the fatty acid distribution in terms of saturated, mono unsaturated and polyunsaturated is essential for the end use of the vegetable oil. The vegetable oil may be extracted from many different products including, but not limited to olive, soybeans, rape seeds, nuts, cacao, palm etc. The following example illustrates how the apparatus can be used to determine the vegetable oil quality from harvest of the fruits, during refinery and as a control unit for the final product.

Figure 6:
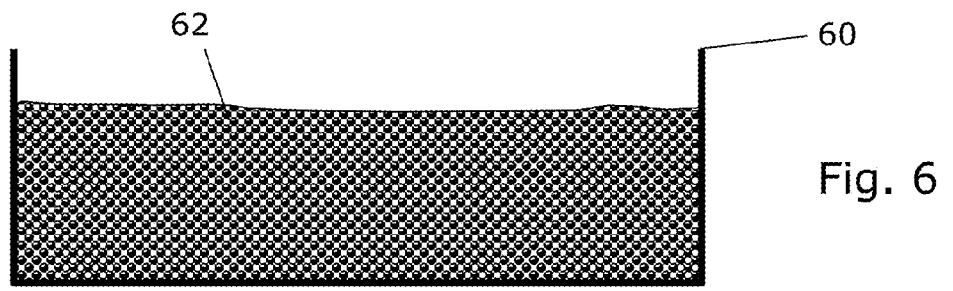
FIGS. 6 and 7 illustrate other inhomogeneous substances.

When olive farmers deliver their harvest to the local refinery, a sample of olives is collected and placed in special designed cylinder. FIG. 6 shows a container 60 filled with particles 62, and can embody such cylinder with olives. The apparatus equipped with probe arms having sharp knives (see e.g. probe arm 6 of FIG. 2) can then be pressed into the cylinder and based upon absorbance of a known number of single olives, the average fatty acid distribution can be determined. This information can be used downstream to sort the olives in different classes and upstream to pay the olive farmer according to weight and quality.

During the process of extracting the vegetable oil from the olives, the apparatus can be used to determine the fatty acid quality of each batch. Based upon this information, the refinery can then make a decision to mix different batches in order the meet the technical specification of the final product. Consequently, determination of vegetable oil quality can be made online without removing a sample for analysis at a centralized laboratory.

Feed for Animal

In recent years, most animal feed is manufactured by large centralized plants using a large number of different raw materials like cereals, soybeans, fish meal, animal fat, milk powder, vitamins, micro minerals etc. According to the predefined recipe of a specific animal feed and the actual costs pattern of the raw materials, each plant optimises the production by the aid of statistical models like linear programming.

According to different national regulations, the feed plant is always obliged to meet the technical specification in terms of chemical and/or physical composition of the feed. The chemical parameters to be determined may include but not limited to content of moisture, protein, fat, ash, crude fiber, carbohydrates in terms of starch, glucose, dextrose etc, vitamins, micro minerals etc. During the production of feed, all raw materials are milled in order to obtain a uniform particle size and thereafter mixed before the final feed is made into pellets. After mixing has taken place, the feed has a physical appearance like a powder, but from a microchemical point of view, the feed is inhomogeneous. FIG. 6 illustrates a container 60 filled with feed powder particles 62.

By inserting the apparatus into the feed powder, the actual chemical composition can be determined because all major components have specific absorbance bands in the infrared light range of 800 nm to 3,000 nm. The insertion may take place in the mixer, silos, pipes etc. The path of measurement with the apparatus can be designed to provide a representative result of the feed powder. The apparatus can also be used to determine the chemical composition of each raw material in a similar way.

Consequently, the feed plant will be able to obtain online information of the final product and of each raw material without the need to send a sample to a centralized laboratory for chemical analysis.

Building Materials

The method and the apparatus have applications in a large number of industries and the following example illustrates the use outside the food industry. In the production of plaster determined as a building material, the moisture content is a vital parameter for the quality of the final product. Initially, the plaster is inhomogeneous and behaves like a gel due to the high content of moisture. At this stage, it is vital to determine the moisture content very accurate and this can be accomplished with the present method and apparatus, because water has a strong absorbance band at 1940 nm. Consequently, the plaster industry will be able to measure moisture online and thereby secure a uniform and high quality of the final plaster, without the need to send samples to a centralized laboratory.

Cheese

Figure 7:
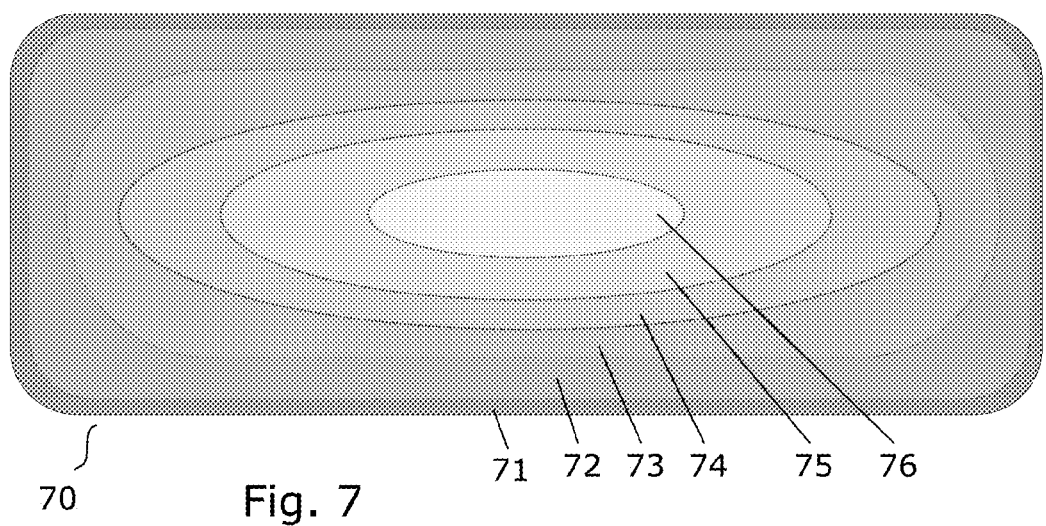

In the fabrication of cheese, the initial chemical composition in terms of total fat, fatty acid distribution of saturated, mono-unsaturated and poly-unsaturated, protein, moisture etc. is very important for the quality of the final product. After treatment of the milk with enzymes, the cheese fraction is compressed to the desired form, and at this stage the immature cheese is inhomogeneous, consisting of compressed fat/protein particles. FIG. 7 is a cross sectional view of a cheese having layers 71-76.

Without any damage to the cheese or without removing a sample of the cheese, the present apparatus is able to determine the initial chemical composition with high accuracy because the determination is made over a path of for instance 10 to 50 cm and the average chemical composition can be calculated.

During the processing of the final cheese, aromatic and flavor compounds are formed. The compounds consist mainly of $—NH_2$ groups with specific absorbance bands in the range of infrared light at 800 nm to 3000 nm. During the maturing process of the cheese, which may be as long as one year, the chemical reactions caused by the specific microorganism may not be uniform with respect to time and location in the cheese. Consequently, there is a need to determine the stage of matureness without making any damage to the final cheese or without removing a sample for chemical analysis in a centralized laboratory.

During the entire process of a specific cheese, the invention is able to provide relevant information of the mature stage of the cheese. Furthermore it is possible to develop a mature profile for each type of cheese which can be used by the cheese factory to secure and monitor that the process follows a predefined pattern.

The data processing in a preferred embodiment of the data processing unit 14 of FIG. 1 will be described in relation to the cheese example in the above.

FIG. 8 is a three-dimensional graph 80 showing absorption spectra covering wavelength ranges from 800 nm to 2500 nm taken at different depths in a cheese 70 of FIG. 70. This is a presentation of the data received by the data processing unit 14 from the spectroscope 12 and the means 18 for determining position.

Figure 10:
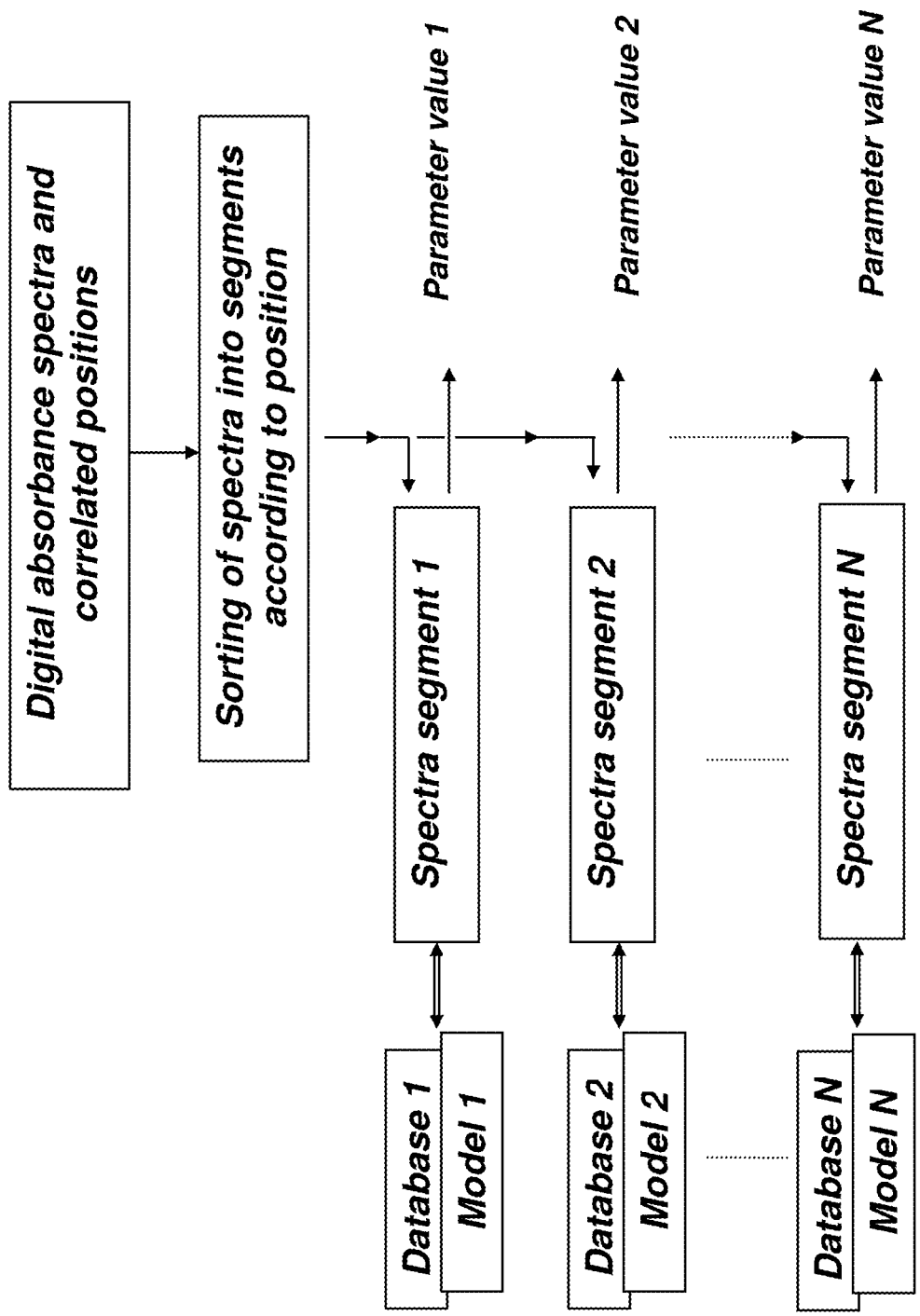
FIG. 10 is a chart illustrating the data processing in the data processing unit.
Figure 11:
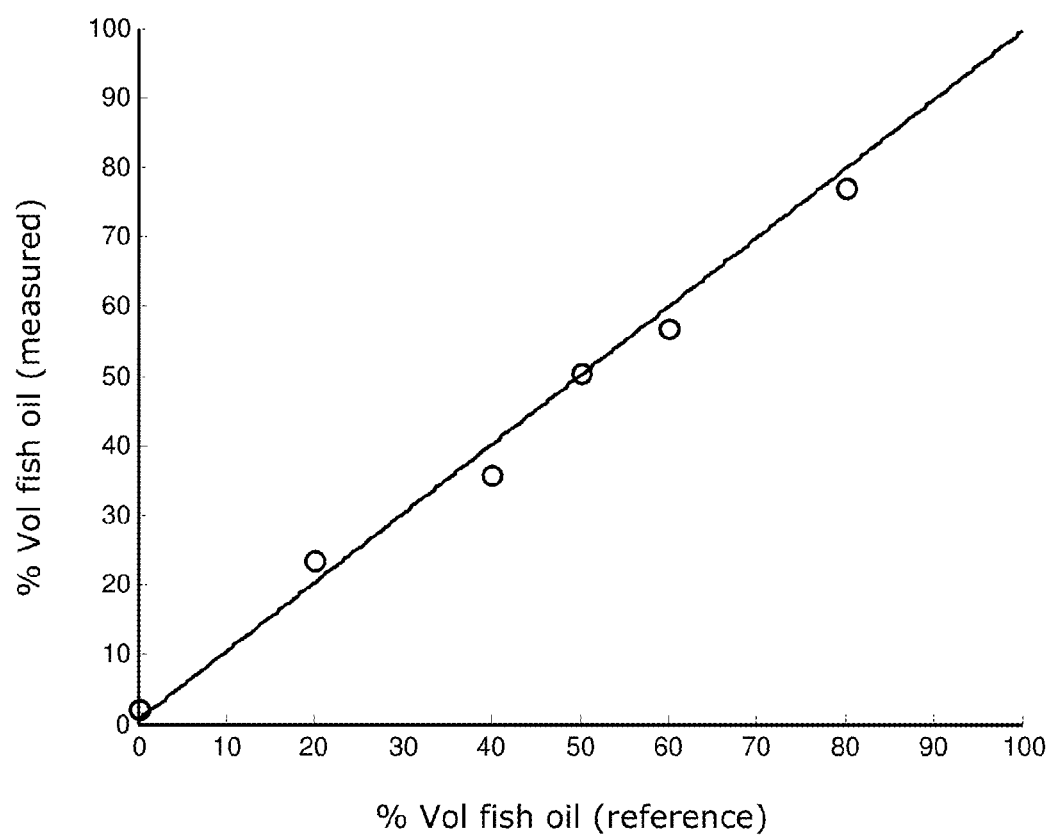
FIG. 11 is a graph illustrating chemometrical determination of volumetric concentration of fish oil in an olive oil based on NIT measurements.

The data shown in graph 80 can be pre-processed before comparison with spectra from databases in the memory 19 of the data processing unit. The pre-processing consists of sorting the spectra into segments so that a batch of spectra in a segment can be used to extract relevant parameters. The pre-processing and sorting of spectra into segments are illustrated in FIG. 10.

Figure 9:
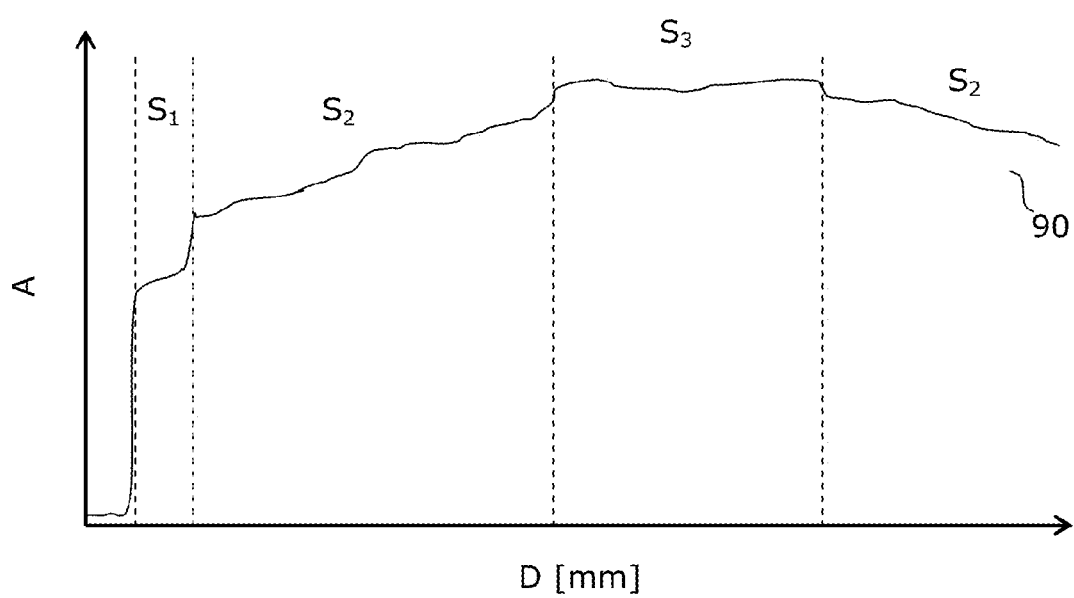
FIG. 9 is a graph showing absorption as a function of depth for a specific wavelength.

One example of this segmentation is described in relation to FIG. 9. Here, a graph 90 illustrates absorption A (arbitrary units) in cheese 70 of FIG. 7 as a function of depth in millimeters for a fixed wavelength $\lambda$ in the range 1,900-1,980 nm. This corresponds to a slice parallel to the depth axis in the graph 80 of FIG. 8.

Water has a prominent absorption in the wavelength range 1,900-1,980 nm, and wavelengths in this range can therefore be used to determine the ripeness or drying of cheese. Before curing, cheese curd is typically encapsulated in a wax 71 to ensure a uniform shape and to reduce or slow down the loss of water during the curing process. In cheese like brie and camembert, the centre core 76 of the cheese can be fluid even when the cheese is ready for consumption. Outer layer 72 will dry out reasonably fast, whereas intermediate layers 73, 74 and 75 will slowly become dryer and firmer during the curing process.

Graph 90 can be divided into segments $S_1$-$S_3$ according to the strength of the water absorption at the applied wavelength. In the given example, segments correspond to different states of ripeness in cheese 70:
  $S_1$: crust/wax
  $S_2$: ripe/dry cheese
  $S_3$: fluid cheese curd By analyzing graph 90, the data processing unit 14 can determine insertion depth intervals corresponding to these segments. The final insertion depth intervals may be determined using average values from a number of graphs similar to graph 90, but for different wavelengths in the range of water absorption. When the region $S_2$ appears again at the right side of graph 90 it means that the probe has passed though the core 76. Hence, it is the absorption level in a predefined wavelength range which defines which segment a cheese porting falls into. Thereby, all spectra recorded in layers with certain water content are grouped in one segment regardless of their position in the cheese.

The size of the segments and the position of the transition between segments can be compared with results from previous laboratory measurements from a database in memory 19.

Using e.g. parafac models, a parameter value for the drying process can be determined, and e.g. an estimated remaining curing time be given.

Another way to estimate the ripeness is to monitor the bacterial processes from rennet in the curd. By choosing wavelengths in the specific absorbance bands for —$NH_2$ groups, a concentration of the relevant molecules can be determined in segments or throughout the cheese. By modeling these data to previously calibrated concentrations from a database, a parameter value for the ripening progress of the cheese can be determined in a way similar to the drying progress explained above. These processes are illustrated in FIG. 10.

The following example illustrates quantitative determination of —$SH_2$ groups in the ripe/dry cheese segment S2. Firstly, an average spectrum for segment S2 is formed by adding absorbance values for each wavelength from the multitude of spectra in the segment.

$$\overline{A}_1 = (A_1^1 + A_1^2 + \ldots + A_1^n)/N$$
$$\vdots$$
$$\overline{A}_m = (A_m^1 + A_m^2 + \ldots + A_m^n)/N$$

wherein $A_m^n$ is the absorbance at wavelength m in the n'th spectrum of the ripe/dry cheese segment S2, and N is the number of spectra in the segment. The average spectrum in segment S2 is then formed by the series of average absorbance values $\overline{A}_1, \overline{A}_1, \overline{A}_1$.

The content Y of —$SH_2$ groups in the ripe/dry cheese segment S2 may then be calculated from $$Y = k_0 + k_0 \cdot \overline{A}_1 + k_2 \cdot \overline{A}_2 + \ldots + k_n \cdot \overline{A}_m,$$

where $k_0, k_1, k_2, \ldots, k_n$ are constants previously determined by a regression model, like partial least square (PLS) and/or principal component analysis (PCA), between NIT spectra in the ripe/dry cheese segment S2 and laboratory analysis data of correctly matured cheeses. The regression model is based upon a given number of samples, e.g. 100 samples.

The parameter values calculated for the different segments and for the different approaches (drying, ripeness) can be used as input to a model for predicting an overall characterization or classification of the curing progress for the cheese. A multivariate model can be used if a linear relationship between the parameter values exists. In cases where the relationship between the absorbance spectra and the chemical analysis data is not linear, the regression models partial least square (PLS) and principal component analysis (PCA) can be combined with neural networks in order to compensate for the non linear relationship. The output may e.g. be an estimated remaining curing time.

An example the ability of NIT measurements for characterizing fatty acid composition is described in the following in relation to FIG. 8. The example measures volumetric concentration of fish oil in an olive oil mixture. The two types of oils are used since they each contain very different concentrations of different types of fatty acids.

Samples are prepared with known concentrations of fish oil in olive oil, 0%, 10%, 30%, 50%, 70%, 90% and 100% are used. NIT is performed on each sample in the area 1100-2200 nm, where several recordings are made on each sample to check for inconsistencies in the measurements. The spectral data are corrected against dark and full-scale references. A PLS model is used to predict the volumetric concentration, using a subset of the measured spectral wavelengths.

A new set of samples is prepared, this time 0%, 20%, 40%, 50%, 60% and 80% and 100% concentrations. Spectrographic data from NIT measurements on these samples are fed to the above model, and measured concentrations are predicted. The results are presented in the graph of FIG. 8, and expresses a R=0.99 with a RMSEP of 3.2 Vol % on the samples unknown to the model.

This example demonstrates the strength of NIT measurements combined with chemometrical analysis, and shows that a detailed knowledge of the fatty acid composition at each position in a product can be obtained using the consecutive NIT spectra according to the present invention.

The invention claimed is:

1. An apparatus for recording of wavelength absorption spectra in a substance, the apparatus comprising
   a probe for penetrating into the substance, the probe having light transmitting means and light receiving means for receiving light transmitted from the light transmitting means, the light transmitting means and the light receiving means defining an optical path of light between the light transmitting means and the light receiving means, the probe being shaped so that when the probe is inserted into the substance an interior portion of the substance at a depth corresponding to the insertion depth of the probe will be received in the optical path
   a means for determining the insertion depth of the probe in the substance, comprising a support for abutting an exterior portion of the substance and a stepping motor operating on the support, when the support abuts against the exterior portion of the surface, for extracting the probe from an inserted position, wherein the insertion depth is determined relative to the support during extraction of the probe;
   a light source for providing infrared light of multiple wavelengths to the light emitting means and
   a detecting unit for detecting wavelength spectra of light received by the light receiving means.

2. The apparatus according to claim 1 wherein the probe is a cutting probe with a sharp end portion for penetrating a surface of a product.

3. The apparatus according to claim 1, further comprising a data processing unit for receiving detected wavelength absorption spectra and being configured to determine qualitative and/or quantitative parameters of the substance, the data processing unit comprising a memory for holding a database of wavelength spectra previously detected on similar substance portions with known qualitative and/or quantitative parameters, and means for comparing detected spectra with spectra from the database to identify at least approximate qualitative and/or quantitative parameters of corresponding interior portions of the substance.

4. The apparatus according to claim 3, wherein the data processing unit is configured to provide the qualitative and/or quantitative parameters as a function of insertion depth.

5. The apparatus according to claim 3, wherein the data processing unit comprises software configured to perform in-situ spectra-based grading of the substance.

6. The apparatus according to claim 1, further comprising a data processing unit for receiving detected wavelength absorption spectra and being configured to determine a content of a predefined substance in the substance, the data processing unit comprising a memory for holding a database of wavelength spectra previously detected on similar substance portions with known contents of the predefined substance, and means for comparing detected spectra with spectra from the database to determine the content of the predefined substance in corresponding interior portions of the substance.

7. The apparatus according to claim 1, wherein the apparatus is interfaced with a system configured to perform online spectra-based grading of the substance.

8. The apparatus according to claim 1, further comprising a means to correlate a determined insertion depth or a change in insertion depth with a detected wavelength absorption spectrum and to trigger recording of a wavelength absorption spectrum for every extraction step of the probe.

9. The apparatus according to claim 1, wherein a first surface part of the probe is an optical window through which light from the light transmitting means will exit the probe, and an opposite second surface part of the probe is an optical window through which light from the light emitting means will enter the probe to be received by the light receiving means.

10. The apparatus according to claim 9, wherein the first and second surface parts are surface parts of the first and second knife, respectively, and wherein a distance between the optical windows of the first and second knives is at least substantially the same as a distance between the points of the first and second knives.

11. The apparatus according to claim 1, wherein the probe comprises a first knife holding the light transmitting means and a second knife holding the light receiving means, the first and second knives extending in parallel from a common base and each having a point for penetrating a surface and a first cutting edge starting at the point.

12. The apparatus according to claim 11, wherein the cutting edges of the first and second knives can be projected onto the same straight line.

13. The apparatus according to claim 1, wherein the probe is formed in a material composition and dimensioned to ensure a constant distance between the light emitting means and the light receiving means during insertion in the substance.

14. The apparatus according to claim 1, wherein the detecting unit is configured to record a spectrum of infrared light received from the light receiving means at user determined intervals when the means for determining insertion depth of the probe indicates that there is no interior portion of a meat product in said optical path between the light emitting means and the light receiving means.

15. A method for recording infrared wavelength absorption spectra in a substance, the method comprising:
   providing an apparatus comprising a probe for penetrating into the substance, the probe having light transmitting means for transmitting infrared light and light receiving means for receiving light transmitted from the light transmitting means, an optical path of light being defined between the light transmitting means and the light receiving means, the probe being shaped so that when the probe is inserted into the substance an interior portion of the substance at a depth corresponding to the insertion depth of the probe will be received in said optical path, the apparatus further having a support for abutting an exterior portion of the substance and a stepping motor operable on the support and configured to change the position of support relative to the probe;
   inserting the probe into the substance to a first insertion depth so as to receive a first interior portion of the substance in said optical path and so that the support abuts an exterior portion of the substance;
   operating, while the support abuts the exterior portion of the substance, the stepping motor to withdraw the probe from the substance so as to change the insertion depth of the probe in the substance to a second insertion depth so as to receive a second interior portion of the substance in said optical path
   determining the second insertion depth of the probe as a distance relative to the support;
   transmitting infrared light of multiple wavelengths from the light transmitting means;
   receiving light transmitted from the light transmitting means; and
   recording a wavelength absorption spectrum of light received by the light receiving means.

16. The method according to claim 15, wherein the substance is a meat product.

17. The method according to claim 15, wherein inserting the probe into the substance is performed in situ so that no sample is removed from the substance.

18. The method according to claim 15, further comprising the step of performing an online grading of the substance based on the detected series of spectra.

19. The method according to claim 15, wherein the step of changing an insertion depth of the probe is a stepwise reduction of the insertion depth so that spectra are stepwise detected during extraction of the probe from the substance.

20. The method according to claim 15, further comprising the step of comparing detected wavelength absorption spectra with wavelength absorption spectra previously detected on substance portions with known qualitative and/or quantitative parameters to determine corresponding qualitative and/or quantitative parameters of the portion(s) used in the recording.

21. The method according to claim 15, further comprising the step of comparing detected wavelength absorption spectra with wavelength absorption spectra previously detected on substance portions with known contents of a predefined substance to determine a content of the predefined substance in the portion(s) used in the recording.

22. The method according to claim 15, further comprising the step of pre-processing detected wavelength absorption spectra to sort spectra into segments and merging, or forming mean values of, spectral data in a segment.

23. The method according to claim 22, wherein each segment corresponds to one or more insertion depth intervals in the substance and wherein spectra are sorted according to their corresponding insertion depth.

24. The method according to claim 23, further comprising the step of using qualitative and/or quantitative parameters from individual segments to determine a grading of the substance.

25. The method according to claim 22, wherein corresponding qualitative and/or quantitative parameters are determined for individual segments.

26. An apparatus for recording a wavelength absorption spectra in a substance, comprising:
   a housing that comprises a light source and a probe, which comprises a transparent window
   an optical fibre that receives and transmits light from the light source to a collimator, which forms directional light deflected by a mirror and transmitted by said transparent window
   a detecting unit, which detects absorption spectra received from the optical fibre
   a support that abuts an exterior portion of the substance
   a stepping motor operating on the support, which can extract the probe from an inserted position by pushing the support against the exterior portion of the substance and
   a position calculation unit that determines the depth of the probe in said substance during extraction of the probe from the inserted position.

* * * * *